United States Patent
Fodor et al.

(10) Patent No.: US 9,057,691 B2
(45) Date of Patent: Jun. 16, 2015

(54) FUEL CELL HOUSING FOR USE IN AN ALCOHOL BREATH TESTER

(71) Applicant: Alcotek, Inc., St. Louis, MO (US)

(72) Inventors: Joe Fodor, Fenton, MO (US); Karl R. Wolf, Jr., Eureka, MO (US)

(73) Assignee: Alcotek, Inc., St. Louis, MO (US)

( * ) Notice: Subject to any disclaimer, the term of this patent is extended or adjusted under 35 U.S.C. 154(b) by 289 days.

(21) Appl. No.: 13/778,786

(22) Filed: Feb. 27, 2013

(65) Prior Publication Data

US 2014/0034492 A1  Feb. 6, 2014

Related U.S. Application Data

(60) Provisional application No. 61/679,629, filed on Aug. 3, 2012.

(51) Int. Cl.
*G01N 27/407* (2006.01)
*A61B 5/097* (2006.01)
*G01N 33/497* (2006.01)

(52) U.S. Cl.
CPC ............ *G01N 27/4078* (2013.01); *A61B 5/097* (2013.01); *G01N 33/497* (2013.01)

(58) Field of Classification Search
CPC . G01N 33/4972; G01N 27/4078; A61B 5/097
See application file for complete search history.

(56) References Cited

U.S. PATENT DOCUMENTS

| | | | |
|---|---|---|---|
| 4,487,055 A * | 12/1984 | Wolf | 73/23.3 |
| 5,291,898 A * | 3/1994 | Wolf | 600/532 |
| 5,759,368 A | 6/1998 | Kuhn | |
| 6,923,040 B2 * | 8/2005 | Stock | 73/23.3 |
| 6,967,581 B2 | 11/2005 | Karsten | |
| 7,855,027 B2 | 12/2010 | Bayer et al. | |
| 7,895,878 B1 * | 3/2011 | Guth et al. | 73/1.03 |
| 8,161,793 B2 * | 4/2012 | Mitchell | 73/23.3 |
| 8,176,766 B1 * | 5/2012 | Ruiz et al. | 73/23.3 |
| 2005/0241871 A1 * | 11/2005 | Stewart et al. | 180/272 |
| 2006/0032742 A1 | 2/2006 | Babes-Dornea et al. | |
| 2007/0154765 A1 * | 7/2007 | Bayer et al. | 429/34 |
| 2007/0173731 A1 * | 7/2007 | Meka et al. | 600/543 |
| 2008/0009693 A1 | 1/2008 | Hawthorne et al. | |

(Continued)

FOREIGN PATENT DOCUMENTS

KR   20110029749 A   3/2011

OTHER PUBLICATIONS

"Alco-Sensor FST Operators Manual," Intoximeters, Inc., http://crwlawyers.com/alco-sensor%20FST%20manual.pdf, Sep. 2004, 29 pages.

(Continued)

*Primary Examiner* — Randy W Gibson
*Assistant Examiner* — Natalie Huls
(74) *Attorney, Agent, or Firm* — Lewis Rice LLC

(57) ABSTRACT

An alcohol fuel cell sensor and the resultant alcohol breath tester assembly. The disclosed housing creates an alcohol breath tester assembly that protects the electrode sensor from liquid ingress, maximizes the sample contact with the platinum electrode surface, and provides a smooth path facilitating laminar flow of the sample through the sensor. This, in turn, provides good flushing of the volume without creating eddies or other turbulence. Additionally, the housing can utilize a vapor barrier layer in the assembly and restricts the layer from touching the electrode surface.

24 Claims, 9 Drawing Sheets

(56) References Cited

U.S. PATENT DOCUMENTS

| | | |
|---|---|---|
| 2010/0173215 A1 | 7/2010 | Chou et al. |
| 2011/0079073 A1* | 4/2011 | Keays ............................. 73/23.3 |
| 2011/0283770 A1* | 11/2011 | Hok ............................... 73/23.3 |
| 2012/0174651 A1 | 7/2012 | Mitchell |
| 2014/0358019 A1* | 12/2014 | Johnson ........................ 600/532 |

OTHER PUBLICATIONS

International Search Report, International Patent Application No. PCT/US13/52492, mailed on Oct. 31, 2013, 11 pages.

International Search Report, International Patent Application No. PCT/US13/51442, mailed on Oct. 16, 2013, 10 pages.

* cited by examiner

FUEL CELL HOUSING FOR USE IN AN ALCOHOL BREATH TESTER

CROSS REFERENCE TO RELATED APPLICATION(S)

This application claims the benefit of U.S. Provisional Patent Application Ser. No. 61/679,629, filed Aug. 3, 2012, the entire disclosure of which is herein incorporated by reference.

BACKGROUND

1. Field of the Invention

This disclosure relates generally to devices for estimating blood alcohol content from a breath sample, and more particularly, to housings for assemblies that utilize a fuel cell for estimating blood alcohol content from a breath sample.

2. Description of the Related Art

An alcoholic beverage is a drink containing ethanol, commonly known as alcohol, although in chemistry the definition of alcohol includes many other compounds. Alcohol, specifically ethanol, is a psychoactive drug and is a powerful central nervous system depressant with a range of side effects.

Alcohol has a biphasic effect on the body, which is to say that its effects change over time. In the initial stages of intoxication, alcohol generally produces feelings of relaxation and cheerfulness. Further consumption however affects the brain leading to slurred speech, blurred vision, clumsiness and delayed reflexes, among other coordination problems. This condition is commonly referred to as intoxication or drunkenness, and eventually subsides when the alcohol has fully metabolized in the body.

When a human drinks alcohol, the alcohol housed in the stomach passes into the bloodstream. Cell membranes are highly permeable to alcohol, so once alcohol is in the bloodstream it can diffuse into nearly every biological tissue of the body. Once in the bloodstream, the alcohol circulates to the brain, resulting in intoxication, loss of inhibition and impairment of motor skills such as driving a vehicle. The amount of alcohol consumed and the circumstances surrounding consumption play a large role in determining the extent of an individual's intoxication. Examples of such circumstances include the amount of food in the stomach at the time of alcohol consumption and the hydration level of the individual at the time of consumption, among others.

Due to the coordination impairment and other symptoms associated with intoxication and drunkenness, most countries have laws against drunk driving, i.e., driving with a certain concentration of ethanol in the blood. The legal threshold of blood alcohol content ranges from 0.0% to 0.08%, depending on the jurisdiction. Punishments for operating a vehicle over the legal limit in a given jurisdiction generally include fines, temporary loss of an individual's driving license and imprisonment. Creation of these laws has led to a market for devices to accurately measure the blood alcohol content of individuals operating motor vehicles.

Blood alcohol content (BAC) or blood alcohol concentration is the concentration of alcohol in the blood (weight per unit volume). While blood alcohol content can be directly measured in a hospital laboratory setting, it is more common for it to be measured in law enforcement situations by estimation from an individual's breath alcohol concentration using a breath alcohol testing machine.

In the world of alcohol-breath testing and related fields of alcohol testing, one of the most common configurations uses fuel cells as alcohol sensors, with the assembly allowing breath, air, gas, or vapor to pass through or into the fuel cell. The fuel cell is generally encased/enclosed in some type of housing which includes two sensor ports—an intake port and a port for a mechanical means for moving the sample through the fuel cell sensor. The mechanical means is generally separate from the fuel cell sensor itself; but such separation is not necessary. In some cases, the mechanical means might only move breath or air in one direction through the fuel cell, as shown in FIG. 1; in other cases, the mechanical means can move the breath/air back and forth in two directions, as shown in FIG. 2.

The mechanical means can take on a variety of forms, including, but not limited to, a diaphragm, a bellow, a piston, or a pump. For example, the mechanical means may be a piston that is able to move a small, fixed volume sample of high accuracy through the sensor in a very short amount of time (e.g., a fraction of a second with the single stroke of a piston) or the piston may use multiple "strokes" to move a larger, less accurate amount of sample over a longer period of time (e.g., a continuous pump operating over several seconds). Moreover, the mechanical means may be connected to the fuel cell by any variety of tubes, connections, or the like and may incorporate any variety of valves, check valves, or directional valves. In any event, the description of the mechanical means here is merely exemplary and not meant to be all-inclusive.

The sensor ports discussed above are generally kept relatively small when compared to the volume of the fuel cell sensor itself. Such a configuration helps isolate the sensor volume from other interior volumes within the assembly and reduces the overall dead space in the assembly.

In its simplest form, the alcohol fuel cell sensor consists of a chemically inert, porous material coated on both sides with thin layers of catalyst such as platinum (forming upper and lower platinum electrode layers). The porous material sandwiched between the two platinum layers contains a liquid acid-electrolyte. Those skilled in the art, however, would understand that the chemically inert porous material, filled with liquid acid-electrolyte, could be replaced by, under certain circumstances, a solid electrolyte element. In any event, the electrolyte allows charges to move between the two electrode layers. Round, platinum wire electrical connections are then applied to the platinum electrodes and connected to an external circuit. As noted above, the entire fuel cell sensor is mounted in a plastic case, which is provided with a gas inlet port that allows a breath sample to be introduced into the assembly. The basic configuration is as described above, and illustrated in FIG. 3.

In the fuel cell sensor, the top platinum electrode (the one closest to the gas inlet) oxidizes any alcohol in the breath sample to produce acetic acid in a 2 step process (ethanol→acetaldehyde→acetic acid) and which also produces free electrons in the process. Hydrogen ions (H+) are also freed in the process, and migrate to the lower platinum electrode of the cell, where they combine with atmospheric oxygen to form water, resulting in a deficiency of electrons on the lower electrode equal to the excess of electrons produced on the upper surface. Because the two electrode surfaces are connected electrically, a current flows through this external circuit to neutralize the charge. With suitable amplification, this current is a precise indicator of the amount of alcohol consumed by the fuel cell, as the number of electrons produced is directly and linearly proportional to the number of alcohol molecules arriving at the catalyst surface. With the number of alcohol molecules, the blood alcohol content can then be determined. This process is illustrated in FIG. 4.

When passing a breath sample into, and especially when passing a sample through the sensor, it is advantageous that the breath sample be spread across as much of the surface of the electrode as possible. This allows the entire electrode surface area to react with the breath sample which results in a more accurate reading. Additionally, when the sample is moved through the sensor, it is important that all the alcohol in the breath sample be attached to the electrode surface for reaction and that none of the key portion of the breath sample (i.e., the alcohol) passes through the sensor without participating in the reaction. This allows for a quicker and more accurate reading on whatever device incorporates the fuel cell sensor for measurement purposes.

There have been attempts in the prior art to ensure the contact between the breath sample and electrode surface area, but they all have their own problems. As shown in FIG. 5, one option is to have the sample intake port offset from the port for the mechanical means. Another option, as shown in FIG. 6, is to use baffles. Generally speaking, these designs do a reasonable job of spreading a fully gaseous, non-condensing sample across the surface of the electrode as discussed above. However, these designs begin to show weakness when the sample contains any liquid.

Breath samples are often contaminated with liquid (e.g., saliva in breath) or create condensation in a sensor due to the extremely high relative humidity of a breath sample (e.g., 34° C. breath sample passing through a sensor with a lower ambient temperature, e.g., 25° C.). Heating the sensor can solve condensation issues at the cost of a more expensive, more complicated design with high energy use when compared to a sensor without heating. Heating the sensor is a less effective strategy when the sample contains actual liquid in the form of large drops which often occurs from those who are intoxicated. Sometimes heating the sensor is not even enough to avoid condensation issues. If condensation occurs in other portions of the breath path that are not heated, liquid might still enter the heated sensor from a prior condensate being forced by the moving gas of the breath into the sensor.

A thin layer (e.g. 5 mil) of gas-permeable membrane or material that is waterproof, thin, stretchable, and compatible with acids (e.g., GORE-TEX®) has been utilized in the prior art to separate the active platinum electrode surface from the remainder of the internal volume of the sensor, as shown in FIG. 7. Generally, the GORE-TEX® layer is placed close to (but not in contact with) the platinum electrode surface to minimize any dead space between the GORE-TEX® and the sensor surface. The GORE-TEX® layer thus serves as a "regulator" to control the rate at which the breath sample reaches the electrode, and to slow down the reaction. It also acts as a moisture barrier such that liquid cannot pass through the membrane to the electrode sensor.

The moisture barrier ensures both that the sensor does not become contaminated with liquid (e.g., saliva in breath) and condensation and that liquid does not enter the electrolyte within the sensor. In these assemblies, the moisture barrier of the GORE-TEX® layer collects the residual liquid and condensation on the surface thereof with the liquid getting "trapped" in the assembly without contacting the electrode. However, a continuously wet area of the GORE-TEX® layer prevents the breath sample from passing efficiently through the GORE-TEX® membrane, can absorb alcohol from, or exude alcohol to, a subsequent gas sample, and ultimately will affect subsequent sensor readings. Moreover, having a GORE-TEX® layer that is sometimes wet and sometimes dry (e.g. depending on how much the breath sensor has been used recently) further affects the sensor accuracy. Therefore, there is a need for an assembly that spreads the sample across the electrode in a predictable fashion and lends itself to easy flushing of this residual liquid and with an efficient and airtight seal for the GORE-TEX® layer to ensure accurate alcohol readings.

SUMMARY

In view of the above described and other problems in the art, disclosed herein is an improved housing for an alcohol fuel cell sensor and the resultant alcohol breath tester assembly. The disclosed housing creates an alcohol breath tester assembly that protects the electrode sensor from liquid ingress, maximizes the sample contact with the platinum electrode surface, and provides a smooth path facilitating laminar flow of the sample through the sensor. This, in turn, provides good flushing of the volume without creating eddies or other turbulence. Additionally, the housing can utilize a vapor barrier layer (e.g., GORE-TEX® or other similar material or membrane) in the assembly and restricts the layer from touching the electrode surface. The system can further provide an air-tight seal at the periphery of the assembly.

There is described herein, among other things, a housing for a fuel cell sensor comprising: a fuel cell sensor having a sensing surface; a lower housing having a top surface and a bottom surface, the lower housing including: a spiral-shaped chamber path spiraling generally about an axis through the top surface and the bottom surface; wherein the spiral-shaped chamber path intersects the top surface and forms a trough open at the top surface; and an upper housing, the upper housing connecting to the top surface; wherein, the fuel cell sensor is encapsulated between the lower housing and the upper housing; and wherein the sensing surface is adjacent the open portion of the trough.

In an embodiment the housing also comprises a pin, the pin attaching the fuel cell sensor tightly to a bottom surface of the upper housing said bottom surface including at least one air cavity.

In an embodiment of the housing, a surface area of the open portion of the trough is about the same as a surface area of the sensing surface.

In an embodiment of the housing, the lower housing further comprises: an intake port from providing gas to the spiral-shaped chamber path; and an exhaust port for taking gas from the spiral-shaped chamber path. The intake port may be connected to a smallest ring of the spiral-shaped chamber path and the exhaust port is connected to a largest ring of the spiral-shaped chamber path or the intake port may be connected to a largest ring of the spiral-shaped chamber path and the exhaust port is connected to a smallest ring of the spiral-shaped chamber path.

In an embodiment of the housing, the sensing surface comprises platinum.

There is also described herein a housing for a fuel cell sensor comprising: a fuel cell sensor having a sensing surface; a lower housing having a top surface and a bottom surface, the lower housing including: a spiral-shaped chamber path spiraling generally about an axis through the top surface and the bottom surface; wherein the spiral-shaped chamber path intersects the top surface and forms a trough open at the top surface; and an intermediate housing including a vapor barrier layer; a clamping pin; an upper housing, the clamping pin holding the fuel cell sensor to the upper housing; wherein, the upper housing is connected to the intermediate housing, the upper housing sealing to a periphery of the vapor barrier layer; wherein the vapor barrier layer contacts the clamping pin; wherein the lower housing connects to the intermediate housing, the lower housing, the intermediate housing, and the upper housing encapsulating the fuel cell; wherein the sensing surface faces the open portion of the trough; wherein the vapor barrier layer is positioned between the sensing surface and the trough; and wherein the vapor barrier layer does not touch the sensing surface.

In an embodiment of the housing, the clamping pin is arranged toward a center of the sensing surface.

In an embodiment of the housing, a surface area of the open portion of the trough is about the same as a surface area of the sensing surface.

In an embodiment of the housing, the lower housing further comprises: an intake port from providing gas to the spiral-shaped chamber path; and an exhaust port for taking gas from the spiral-shaped chamber path. The intake port may be connected to a smallest ring of the spiral-shaped chamber path and the exhaust port is connected to a largest ring of the spiral-shaped chamber path or the intake port may be connected to a largest ring of the spiral-shaped chamber path and the exhaust port is connected to a smallest ring of the spiral-shaped chamber path.

In an embodiment of the housing, the sensing surface comprises platinum.

There is also described herein, a breath alcohol tester comprising: an intake port; an exhaust port; a fuel cell sensor having a sensing surface; a housing for a fuel cell sensor comprising: a lower housing having a top surface and a bottom surface, the lower housing including: a spiral-shaped chamber path spiraling generally about an axis through the top surface and the bottom surface; wherein the spiral-shaped chamber path intersects the top surface and forms a trough open at the top surface; and wherein the spiral-shaped chamber path is in fluid communication with the intake port and the exhaust port; and an upper housing, the upper housing connecting to the top surface; wherein the fuel cell is between the lower housing and the upper housing; and wherein the sensing surface is adjacent the open portion of the trough.

In an embodiment the breath alcohol tester further comprises: an intermediate housing including a vapor barrier layer; and a clamping pin; wherein the clamping pin holds the fuel cell sensor to the upper housing; wherein, the upper housing is connected to the intermediate housing, the upper housing sealing to a periphery of the vapor barrier layer; wherein the vapor barrier layer contacts the clamping pin; wherein the lower housing connects to the intermediate housing, the lower housing, the intermediate housing, and the upper housing encapsulating the fuel cell; wherein the vapor barrier layer is positioned between the sensing surface and the trough; and wherein the vapor barrier layer does not touch the sensing surface.

In an embodiment of the breath alcohol tester, the clamping pin is arranged toward a center of the sensing surface.

In an embodiment of the breath alcohol tester, a surface area of the open portion of the trough is about the same as a surface area of the sensing surface.

In an embodiment of the breath alcohol tester, the intake port and the exhaust port are in the lower housing.

In an embodiment of the breath alcohol tester, the intake port is connected to a smallest ring of the spiral-shaped chamber path and the exhaust port is connected to a largest ring of the spiral-shaped chamber path. Alternatively, the intake port is connected to a largest ring of the spiral-shaped chamber path and the exhaust port is connected to a smallest ring of the spiral-shaped chamber path.

In an embodiment of the breath alcohol tester, the intake port is in fluid communication with an intake passageway that includes a check valve.

In an embodiment of the breath alcohol tester, the sensing surface comprises platinum.

Figure 1:
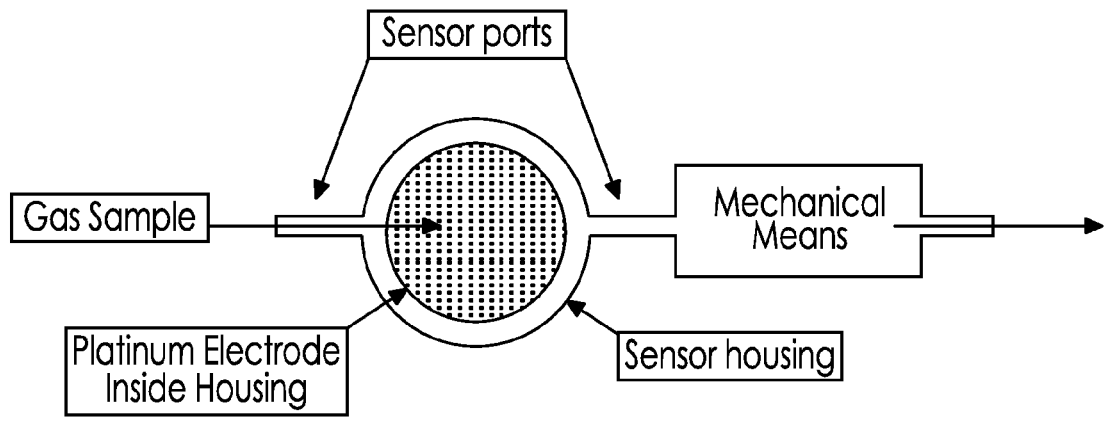
FIG. 1 depicts a basic configuration of an alcohol breath tester assembly including a fuel cell sensor and a mechanical means attached thereto of the prior art.
Figure 2:
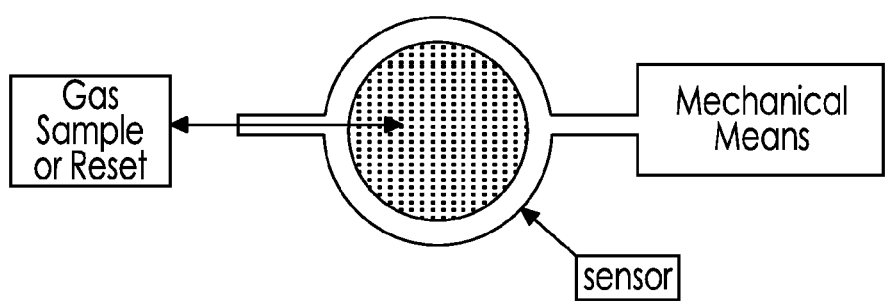
FIG. 2 depicts a prior art assembly similar to FIG. 1 but with the mechanical means allowing for movement of the gas sample in multiple directions.
Figure 3:
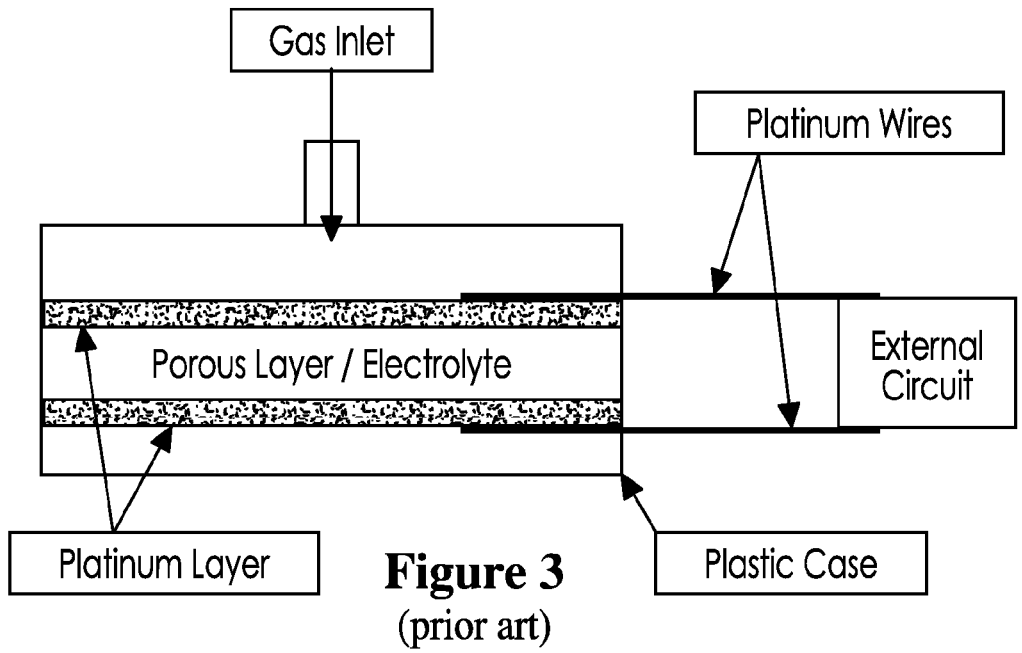
FIG. 3 depicts a basic configuration of a prior art fuel cell sensor and assembly and showing the connection between the platinum wires and an external circuit.
Figure 4:
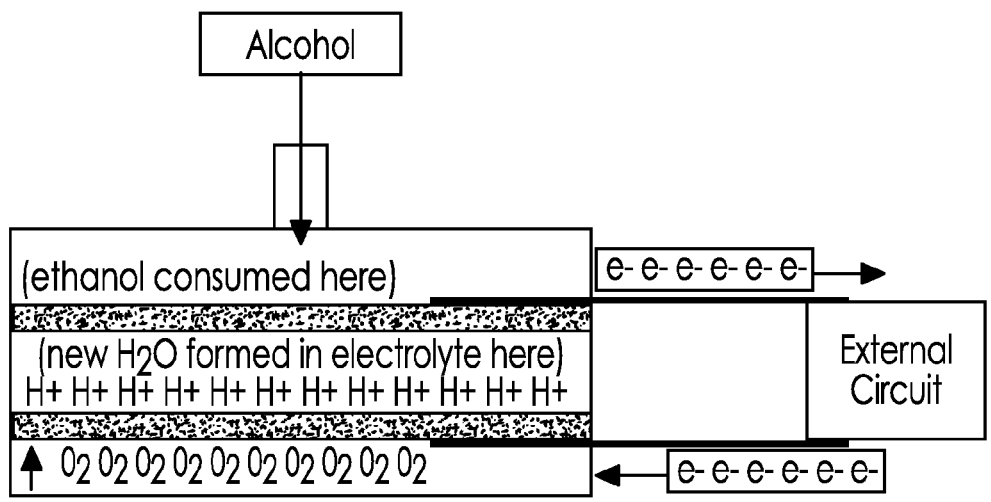
FIG. 4 depicts the sensor and assembly of FIG. 3 and showing the chemical reaction and current flow as alcohol from a breath sample is introduced into the assembly.
Figure 5:
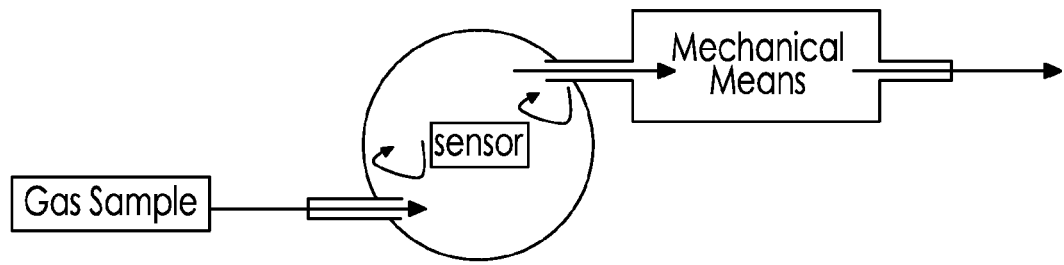
FIG. 5 depicts a prior art assembly with the breath sample intake port offset from the port for the mechanical means and showing the eddies that result from such a configuration.
Figure 6:
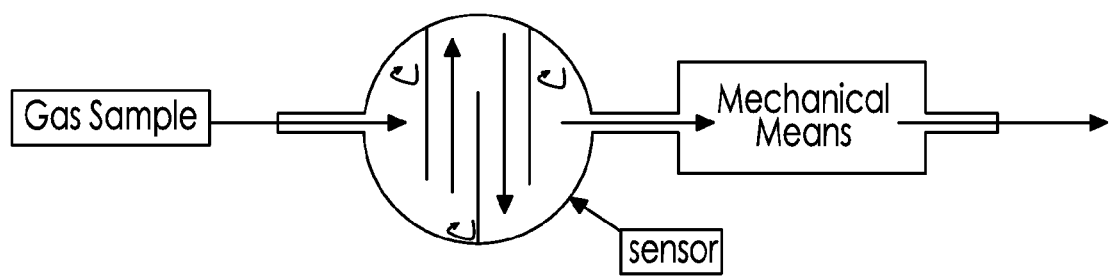
FIG. 6 depicts a prior art assembly with baffles in the housing and showing the eddies that result from such a configuration.
Figure 7:
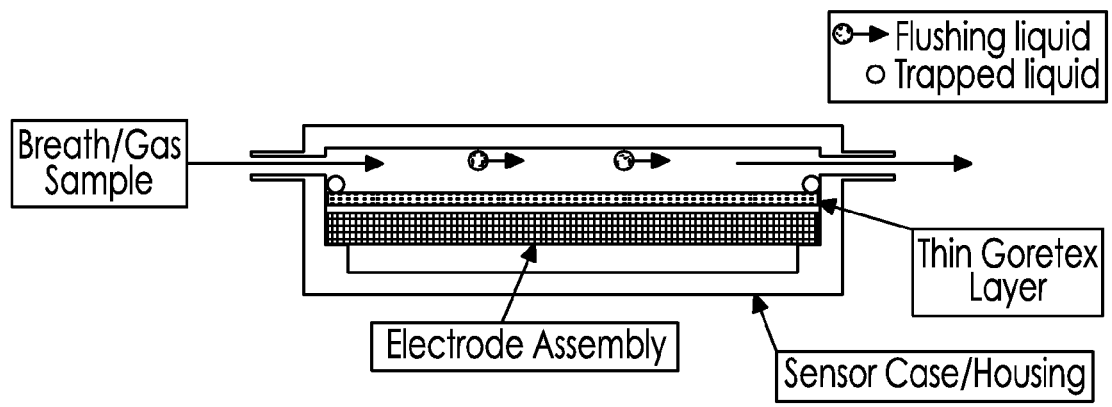
FIG. 7 depicts a basic configuration of a prior art assembly with a vapor barrier layer and the trapped liquid that results in such assemblies.

DESCRIPTION OF PREFERRED
EMBODIMENT(S)

It should be noted the name GORE-TEX® is used throughout this description because of its familiarity to those of ordinary skill in the art as a gas permeable, vapor resistant material. However, this disclosure contemplates any gas-permeable membrane or material that is water resistant (or waterproof), thin, stretchable, and compatible with acids. Water is the most important liquid to be kept from passing through the membrane, however, the membrane may also act as a barrier to other liquids. The gas-permeable membrane may also be selectively permeable to certain gases, such as ethanol.

Turning now to FIGS. 8-14, there is disclosed an alcohol breath tester assembly (101) and associated housing that will be described more fully according to several embodiments. Generally, the assembly (101) comprises a fuel cell sensor (100) enclosed within an upper housing (400), a lower housing (300), and an optional intermediate housing (500).

The fuel cell sensor (100) could be any fuel cell sensor, as that term is commonly understood by those of ordinary skill in the art, now known or later developed for use in an alcohol breath tester assembly. In an exemplary embodiment, the fuel cell (100) will comprise a platinum wafer (200), a clamping pin (110), and two wires ((150a) and (150b)). The wafer (200) generally comprises a porous, chemically inert material coated on both sides with thin layers of platinum (forming platinum electrode layers) and with an acid-electrolyte soaked up in the material sandwiched between the two electrode layers, which allows charges to move between the two electrode layers. The wafer (200) may have a hole (201) near the center for receiving the clamping pin (110), which in turn, receives the wires ((150a) and (150b)) and securely connects the wires ((150a) and (150b)) to the wafer (200). It should be noted that this description is merely exemplary. Fuel cell sensors of other types are known and commonly utilized by those of ordinary skill in the art and such known fuel cell sensors could be utilized with the housing described below.

As noted above, the fuel cell sensor (100) is enclosed within a housing comprising an upper housing (400) and a lower housing (300). As such, the upper housing (400) is sized and shaped to receive the fuel cell sensor (100) and is adapted to be attached to the lower housing (300) as well as an intermediate housing (500), if an intermediate housing (500) is present. In this regard, the upper housing (400) will generally include a hole (410) to allow the wires ((150a) and (150b)) from the fuel cell sensor (100) to exit the upper housing (400) and an indent (420) near the perimeter of the upper housing (400) for accepting the intermediate housing (500) (and vapor barrier layer (600)), as discussed more fully below. As noted, it can be advantageous to install a vapor barrier layer (600) between the electrode wafer (200) and the gas sample path of the lower housing (300) for reasons earlier described and as discussed more fully below.

Figure 11:
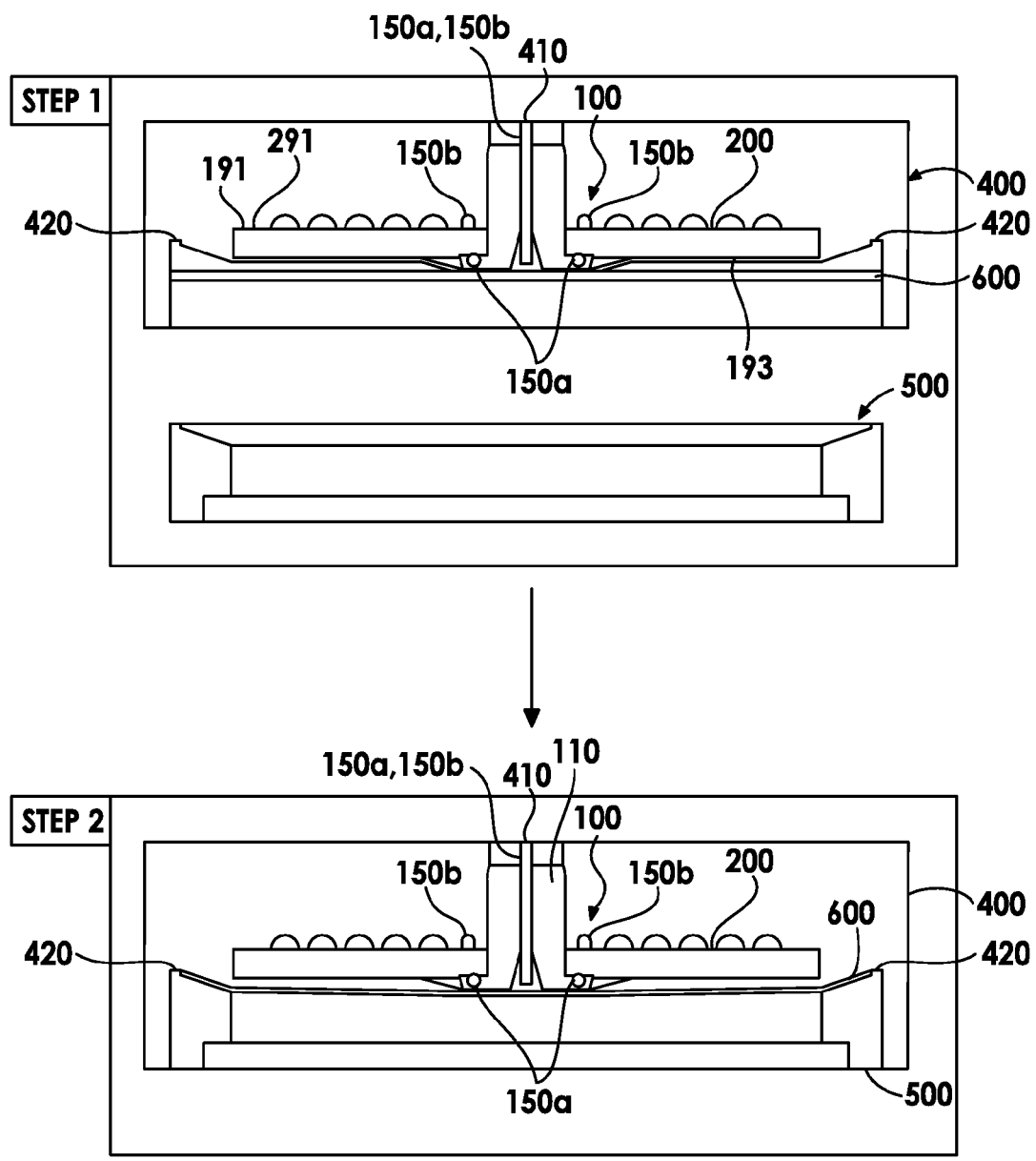
FIG. 11 depicts a cross-sectional view of an embodiment of the upper and intermediate housings and demonstrates the steps for placing the two housings together.

Turning now to FIG. 11, one can see the upper housing (400) and fuel cell sensor (100) as previously described including an electrode wafer (200) with the hole in the middle, and a clamping pin (110) securing the two wires ((150a) and (150b)) to the electrode wafer (200), and securing the electrode wafer (200) to the upper housing (400) at the lower surface (291) which is adjacent to the non-sensing surface (191) of the fuel cell sensor (100). This connection between the lower surface (291) and the non-sensing surface (191) is generally tight, although air cavities (295) may be provided to supply oxygen to the non-sensing surface (191) to ensure the reaction in the fuel cell (100) can progress. In Step 1, a properly sized vapor barrier layer (600) is then laid flat onto the upper housing (400) and the center clamping pin (110), with the vapor barrier layer (600) extending over the indent (420) around the periphery of the upper housing (400). In Step 2, the intermediate housing (500), which is generally in the shape of a ring, is brought into contact with—and secured into the indents (420) of—the upper housing (400). As a result, the vapor barrier layer (600) is captured between the upper housing (400) and the intermediate housing (500). In the process, the vapor barrier layer (600) is slightly stretched across the central pin (100) as well as at its periphery. This ensures that the vapor barrier layer (600) cannot touch the sensing surface (193) of the electrode wafer (200) and that the vapor barrier layer (600) is sealed at its periphery (i.e., at the indents (420) of the upper housing (400)). In this regard, the intermediate housing (500) acts as a compression ring—the entire perimeter of the vapor barrier layer (600) is sealed with the vapor barrier (600) stretched tightly against the surface of center clamping pin (110) while avoiding any contact with the sensing surface (193) of the electrode wafer (200) of the fuel cell sensor (100).

The intermediate housing (500) may be permanently attached to the upper housing (400) by slip fit, press fit, snap fit, glue, heat weld, ultrasonic weld, or the like. Those skilled in the art will understand that other means may be used to attach these parts without changing the nature of the invention. Further, the attachment could be temporarily attached instead of permanently attached.

When completed, this assembly of the upper housing (400), intermediate housing (500) and vapor barrier layer (600) prohibits liquid from penetrating through to the electrode wafer (200) of the fuel cell (100). Further, no gas sample can reach the electrode wafer (200) without first passing through the vapor barrier layer (600), and as a result, liquid from the gas/breath sample cannot reach the cell (100).

Figure 12:
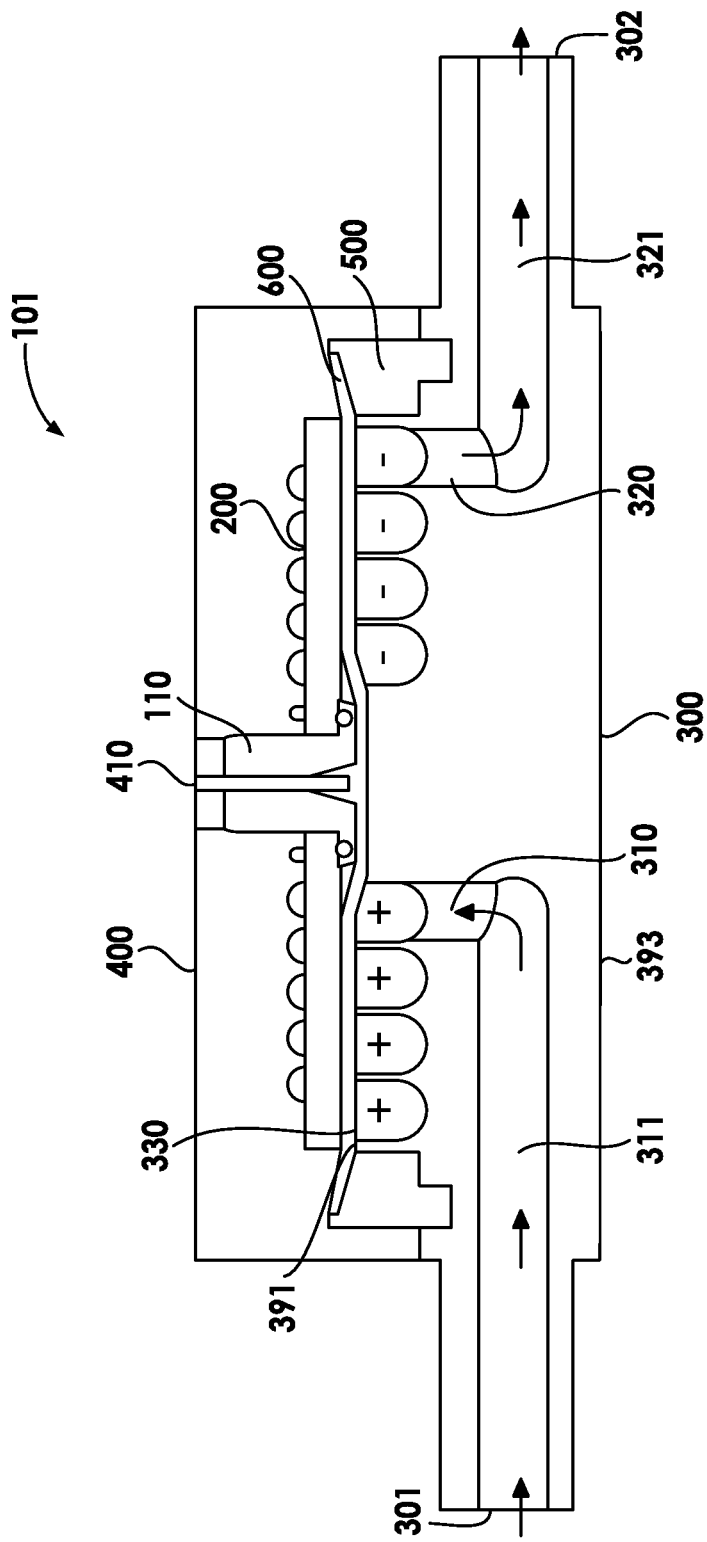
FIG. 12 depicts a cross-sectional view of an embodiment of a final assembly of the alcohol breath tester and shows the upper, lower and intermediate housings assembled together.
Figure 13A:
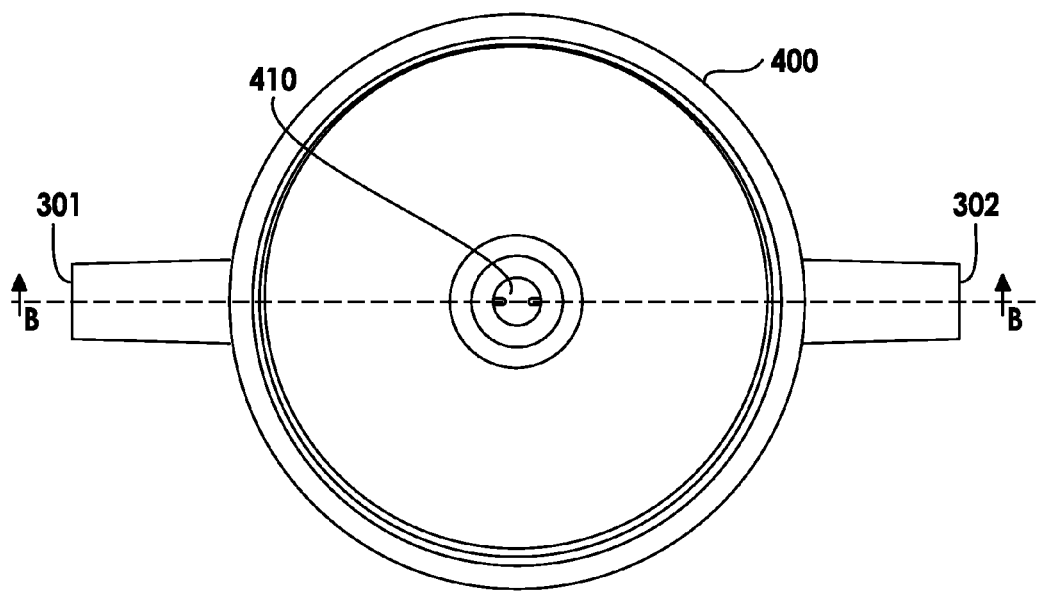
FIG. 13A depicts a top view of an embodiment of a final assembly of the alcohol breath tester.
Figure 13B:
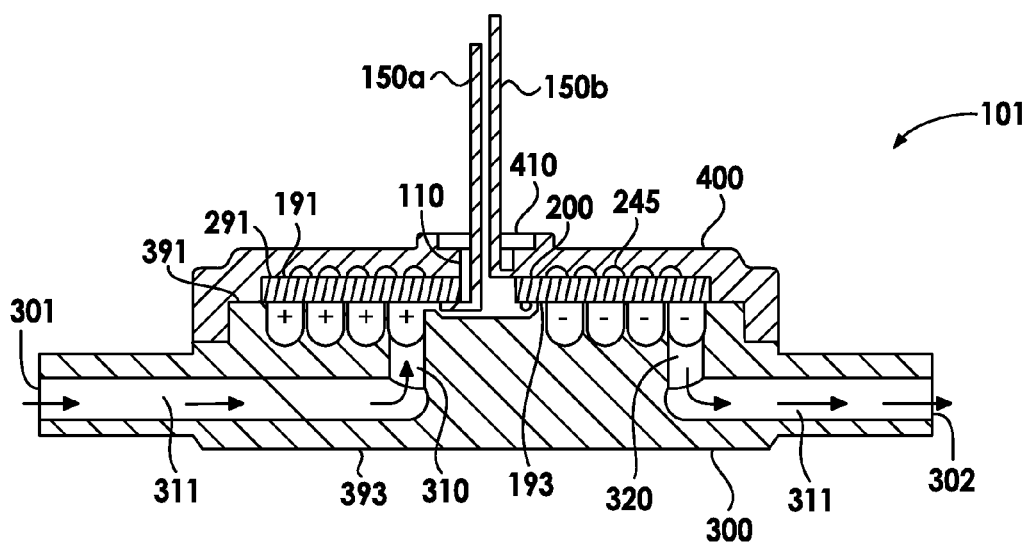
FIG. 13B depicts a cross-sectional view taken along line B.
Figure 14A:
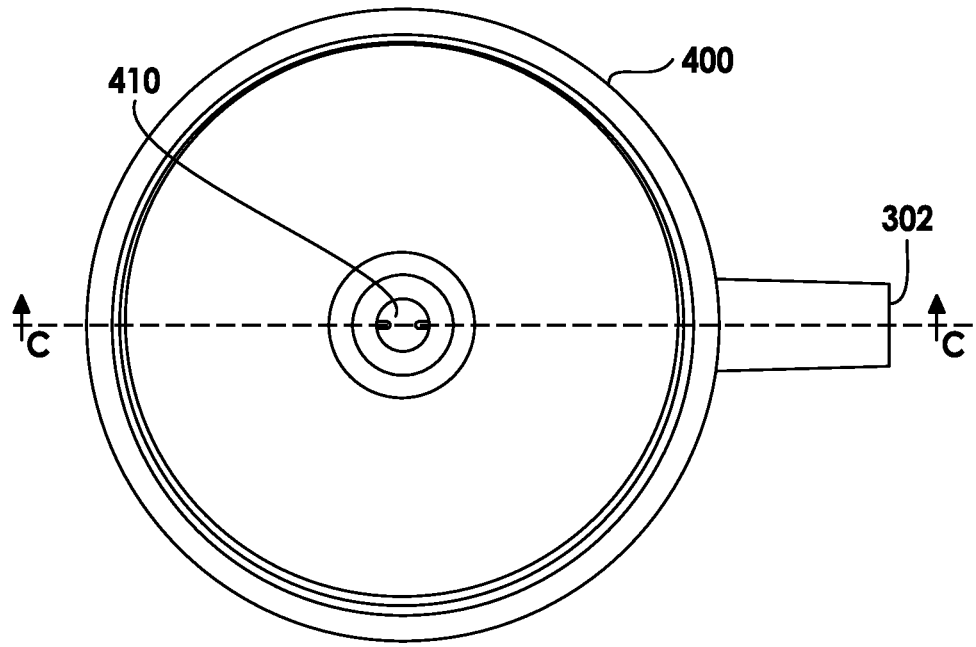
FIG. 14A depicts a top view of an embodiment of a final assembly of the alcohol breath tester.
Figure 14B:
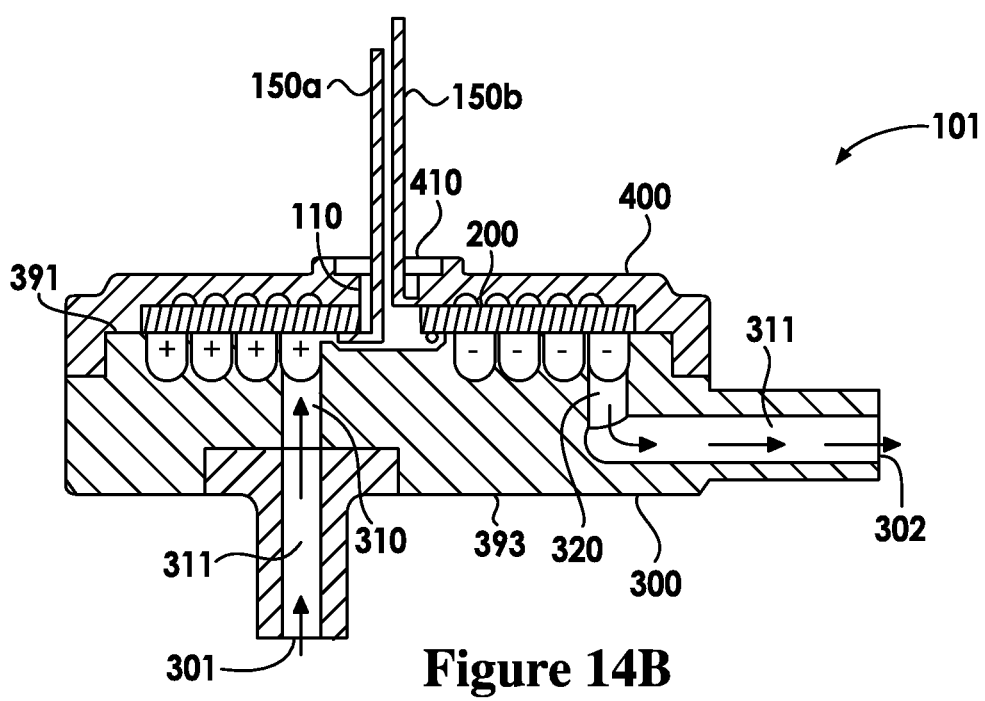
FIG. 14B depicts a cross-sectional view taken along line C.

The lower housing (300) is then attached to the upper housing (400)—and intermediate housing (500) if present—as shown in FIG. 12 (with the intermediate housing (500)) and FIGS. 13-14 (without the intermediate housing (500)). As shown in the embodiment in FIG. 12, the lower housing (300) is brought into contact with the upper housing (400), the intermediate housing (500), and the vapor barrier layer (600). When the lower housing (500) is in final position, it pushes up slightly on the vapor barrier layer (600), ensuring a tight seal between the vapor barrier layer (600) and the top, flat edges of the spiral-shaped chamber path (330), discussed below. This assembly does so while still keeping the vapor barrier layer (600) from contacting the electrode wafer (200). This sealed construction allows for no other path for the gas sample to follow during sample acquisition other than through the spiral-shaped circuitous route, followed by diffusion through the vapor barrier all along that same path. The lower housing (500) may be permanently attached to the upper and intermediate housings ((400) and (500), respectively) by slip fit, press fit, snap fit, glue, heat weld, ultrasonic weld, or the like. Those skilled in the art will understand that other methods and means may be used to attach these parts without changing the nature of the invention. Further, the attachment could be temporarily attached instead of permanently attached.

The embodiment in FIG. 13 is similar to that of FIG. 12 excepting that the embodiment in FIG. 13 does not include the vapor barrier layer (600). In this embodiment, the top, flat edges of chamber path (330) of the lower housing (300) directly contact the surface of the electrode wafer (200). This sealed construction also allows for no other path for the gas sample to follow during sample acquisition other than through the spiral-shaped circuitous route, followed by absorption of the gas to the electrode all along that same route.

Regardless of the use of an intermediate housing (500) or not, any embodiment of the housing may be designed to facilitate recovery from a severe case of liquid ingress into the sensor (100) and/or upper housing (400) and lower housing (300). Specifically the mechanical means used to provide the sample could be used to repeatedly run purge air (for example, ambient air as opposed to a breath sample, or dry air supplied from a canister) through the spiral-shaped path to dislodge and remove any liquid before any subsequent gas sample acquisition and analysis. Effectively, this process uses the mechanical means to supply purge air to dry the pathway by forcing fluid from the spiral-shaped circuitous route and the surface of the vapor barrier layer (600).

FIG. 14 demonstrates an embodiment in which the intake port (301) is shortened and directed differently. Additionally, a check valve could also be inserted at the intake port (301). All such modifications (e.g., shortening and redirecting of the intake port (301)—or the exhaust port (302)—and utilization of a check valve or other valves) could be included with any of the embodiments disclosed herein.

As noted, the lower housing (300) generally includes a spiral-shaped chamber path (330) for the breath sample to follow and pass through with the chamber path (330) placed correspondingly with the electrode wafer (200)—the electrode wafer (200) could be placed tightly against the top of the lower housing (300) as a lid of sorts as shown, for example, in FIG. 13 or the spiral-shaped chamber can be placed against the vapor barrier layer (600) as shown in FIG. 12.

An embodiment of the lower housing is shown in FIGS. 8-10 and 12-14. The lower housing comprises a spiral-shaped chamber path (330) open at the top of the lower housing for the gas/breath sample to travel through or across the fuel sensor (100). In FIGS. 8-10 and 12-14, the flow of gas/breath sample is indicated with arrows (→) and plus (+) and minus (−) symbols (with + indicating flow into the page and − indicating flow out of the page). As can be seen, the gas/breath sample enters at the intake port (301) at the lower level of the lower housing (300) and toward the center of the spiral and continues through a hollow, elongated intake passageway (311). At the end of the intake passageway (311), the gas/breath sample moves perpendicularly through a shorter intermediate passageway (310)—although, as shown in FIG. 14, the intake port (301) and intake passageway (311) could be parallel with the intermediate passageway (310). The gas/breath sample then enters into the chamber path (330) at the higher level of the lower housing (300) and at the interior of electrode wafer (200) via the smallest (most interior) ring. It should be recognized that in an alternative embodiment the intake (301) may be connected to the largest ring.

Figure 8A:
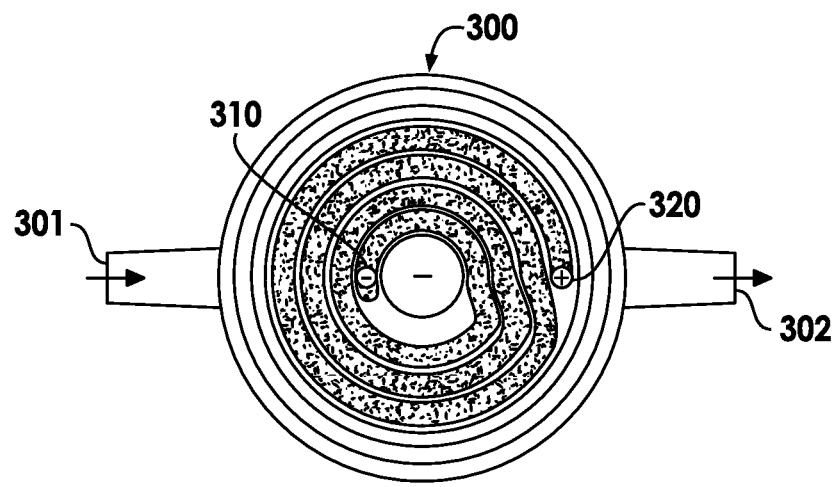
FIG. 8A depicts a top view of an embodiment of the lower housing and showing the spiral path for the breath sample.
Figure 8B:
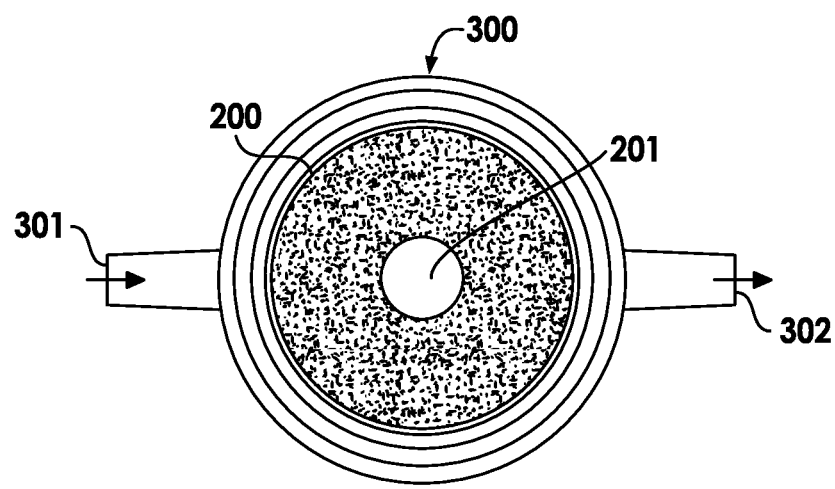
FIG. 8B depicts a top view of an embodiment of the lower housing with an electrode aligned over the lower housing.
Figure 9A:
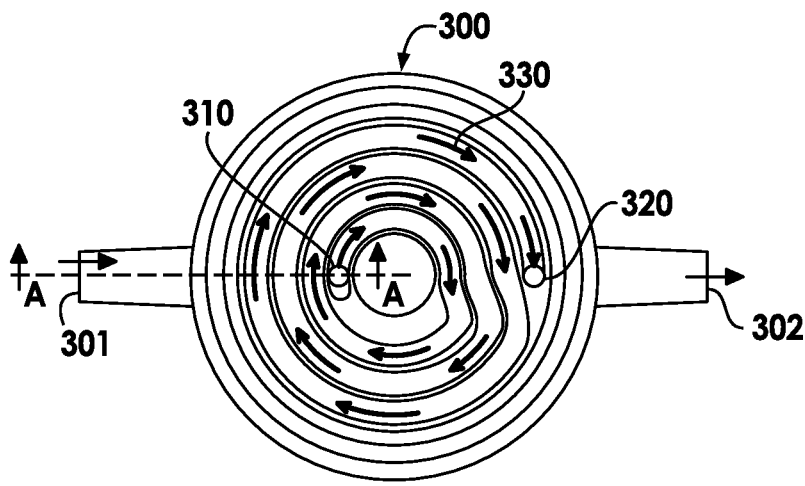
FIG. 9A depicts a top view of an embodiment of the lower housing and showing the spiral path for the breath sample.
Figure 9B:
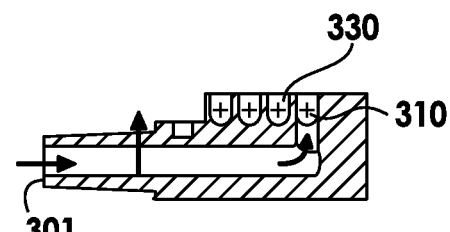
FIG. 9B depicts a cross-sectional view of an embodiment of the lower housing taken along line A in FIG. 9A.
Figure 10:
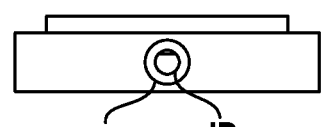
FIG. 10 depicts a side view of an embodiment of the lower housing.

In an embodiment, this path (330) is spiral shaped and is open at the top side creating a spiral trough where the open side (the top) is the same size or approximately the same size as the electrode wafer (200) which allows for maximum surface area contact of gas/breath sample across the electrode wafer (200) and/or vapor barrier layer (600), if present. This is best illustrated in FIGS. 8A and 8B where the open surface at the top (showing the spiral) is visible and the spiral of the path (300) is generally about an axis parallel to the hole (410) and through (and generally perpendicular to) both the top (391) and bottom (393) surfaces of the lower housing (300). At the end of the chamber path (330), which corresponds to the outer diameter of the electrode wafer (200) and the largest ring of the spiral, the gas/breath sample then enters into a second intermediate passageway (320) and then perpendicularly into an outtake passageway (321) at the lower level of the lower housing (300). The gas/breath sample then exits at the exhaust port (302). It should be recognized that in an alternative embodiment the exhaust (301) may be connected to the smallest ring. Additionally, the exhaust port (302) may include a mechanical means attached thereto for actuating the gas/breath sample movement.

In one particular embodiment, the total amount of volume from intake port (301) to exhaust port (302) is 0.264 cubic inches with the volume of the chamber path (330)—the portion directly under the active surface of the fuel cell (100) (i.e., the electrode wafer (200))—having a volume of 0.220 cubic inches and the intake and exhaust ports having inner cross-sectional areas for flow of 0.003 square inches, inner diameters (ID) of 0.060 inches, and outer diameters (OD) of 0.112 inches. As a result, depending on the volume of gas/breath from the sources and flow rate, the chamber path (330) will exchange the gas/breath sample with the wafer (200) several times in one cycle. However, those skilled in the art understand that the exact dimensions, scale, and shapes in the disclosed figures are merely exemplary and could be altered without changing the nature of the invention. Also, the intake and exhaust ports ((301) and (302)) could be designed differently without changing the nature of the invention.

The above described configuration of the chamber path (330) with the electrode wafer (200) provides numerous advantages over the prior art. The path of the sample gas/breath must follow the spiral chamber path (330) before exiting the fuel sensor (100), and in that process, must utilize virtually the entire active surface of the electrode wafer (200) as the open top surface of the chamber path (330) essentially corresponds to the surface area of the electrode wafer (200). Thus, by the time the gas/breath exits the fuel sensor (100), the key constituent of the gas, e.g., ethanol, will have been almost entirely captured by the electrode surface for reaction. Further, the spiral chamber path (330) generally is of equal and uniform cross-sectional area throughout, creating a completely flushable path for the gas/breath so no liquids or contaminants can easily be trapped in flow eddies. In other words, the air flow channel is smooth and continuous maintaining a consistent size orifice from intake to exhaust which facilitates laminar flow of the sample through the sensor. This, in turn, provides good flushing of the volume of the chamber without creating eddies or other turbulence and eliminates any areas prone to trapping air and/or liquid.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, and that the invention will include all embodiments falling within the scope of the appended claims.

It will further be understood that any of the ranges, values, or characteristics given for any single component of the present invention can be used interchangeably with any ranges, values, or characteristics given for any of the other components of the invention, where compatible, to form an embodiment having defined values for each of the components, as given herein throughout.

The invention claimed is:

1. A housing for a fuel cell sensor comprising:
A fuel cell sensor having a sensing surface;
a lower housing having a top surface and a bottom surface, said lower housing including:
  a spiral-shaped chamber path spiraling generally about an axis through said top surface and said bottom surface;
  wherein said spiral-shaped chamber path intersects said top surface and forms a trough open at said top surface; and
an upper housing, said upper housing connecting to said top surface;
wherein, said fuel cell sensor is encapsulated between said lower housing and said upper housing; and
wherein said sensing surface is adjacent said open portion of said trough.

2. The housing of claim 1 wherein a surface area of said open portion of said trough is about the same as a surface area of said sensing surface.

3. The housing of claim 1 wherein said lower housing further comprises:

an intake port from providing gas to said spiral-shaped chamber path; and an exhaust port for taking gas from said spiral-shaped chamber path.

4. The housing of claim 3 wherein said intake port is connected to a smallest ring of said spiral-shaped chamber path and said exhaust port is connected to a largest ring of said spiral-shaped chamber path.

5. The housing of claim 3 wherein said intake port is connected to a largest ring of said spiral-shaped chamber path and said exhaust port is connected to a smallest ring of said spiral-shaped chamber path.

6. The housing of claim 3 wherein said intake port and said exhaust port run perpendicular to each other.

7. The housing of claim 1 wherein said sensing surface comprises platinum.

8. The housing of claim 1 wherein the housing further comprises: a pin, the pin attaching the fuel cell sensor tightly to a bottom surface of the upper housing, said bottom surface including at least one air cavity.

9. A housing for a fuel cell sensor comprising:

A fuel cell sensor having a sensing surface;

a lower housing having a top surface and a bottom surface, said lower housing including:
  a spiral-shaped chamber path spiraling generally about an axis through said top surface and said bottom surface;
  wherein said spiral-shaped chamber path intersects said top surface and forms a trough open at said top surface; and an intermediate housing including a vapor barrier layer;

a clamping pin;

an upper housing, said clamping pin holding said fuel cell sensor to said upper housing;

wherein, said upper housing is connected to said intermediate housing, said upper housing sealing to a periphery of said vapor barrier layer;

wherein said vapor barrier layer contacts said clamping pin;

wherein said lower housing connects to said intermediate housing, said lower housing, said intermediate housing, and said upper housing encapsulating said fuel cell;

wherein said sensing surface faces said open portion of said trough;

wherein said vapor barrier layer is positioned between said sensing surface and said trough; and wherein said vapor barrier layer does not touch said sensing surface.

10. The housing of claim 9 wherein said clamping pin is arranged toward a center of said sensing surface.

11. The housing of claim 9 wherein a surface area of said open portion of said trough is about the same as a surface area of said sensing surface.

12. The housing of claim 9 wherein said lower housing further comprises:
an intake port from providing gas to said spiral-shaped chamber path; and
an exhaust port for taking gas from said spiral-shaped chamber path.

13. The housing of claim 12 wherein said intake port is connected to a smallest ring of said spiral-shaped chamber path and said exhaust port is connected to a largest ring of said spiral-shaped chamber path.

14. The housing of claim 12 wherein said intake port is connected to a largest ring of said spiral-shaped chamber path and said exhaust port is connected to a smallest ring of said spiral-shaped chamber path.

15. The housing of claim 12 wherein said intake port and said exhaust port run perpendicular to each other.

16. The housing of claim 9 wherein said sensing surface comprises platinum.

17. A breath alcohol tester comprising:

an intake port;

an exhaust port;

a fuel cell sensor having a sensing surface;

a housing for a fuel cell sensor comprising:
  a lower housing having a top surface and a bottom surface, said lower housing including:
    a spiral-shaped chamber path spiraling generally about an axis through said top surface and said bottom surface;
    wherein said spiral-shaped chamber path intersects said top surface and forms a trough open at said top surface; and
    wherein said spiral-shaped chamber path is in fluid communication with said intake port and said exhaust port; and
  an upper housing, said upper housing connecting to said top surface;
  wherein said fuel cell is between said lower housing and said upper housing; and
  wherein said sensing surface is adjacent said open portion of said trough.

18. The breath alcohol tester of claim 17 further comprising:
an intermediate housing including a vapor barrier layer; and
a clamping pin;
wherein said clamping pin holds said fuel cell sensor to said upper housing;
wherein, said upper housing is connected to said intermediate housing, said upper housing sealing to a periphery of said vapor barrier layer;
wherein said vapor barrier layer contacts said clamping pin;
wherein said lower housing connects to said intermediate housing, said lower housing, said intermediate housing, and said upper housing encapsulating said fuel cell;
wherein said vapor barrier layer is positioned between said sensing surface and said trough; and
wherein said vapor barrier layer does not touch said sensing surface.

19. The housing of claim 18 wherein said clamping pin is arranged toward a center of said sensing surface.

20. The housing of claim 17 wherein a surface area of said open portion of said trough is about the same as a surface area of said sensing surface.

21. The housing of claim 17 wherein said intake port and said exhaust port are in said lower housing and run perpendicular to each other.

22. The housing of claim 17 wherein said intake port is connected to a smallest ring of said spiral-shaped chamber path and said exhaust port is connected to a largest ring of said spiral-shaped chamber path.

23. The housing of claim 17 wherein said intake port is in fluid communication with an intake passageway that includes a check valve.

24. The housing of claim 17 wherein said sensing surface comprises platinum.

* * * * *